US012697144B2

(12) United States Patent     (10) Patent No.:   US 12,697,144 B2

Flavin     (45) Date of Patent:     Aug. 4, 2026

(54) TALAR REPAIR JIG

(71) Applicant: Tyber Medical LLC, Bethlehem, PA (US)

(72) Inventor: Robert Flavin, Enniskerry (IE)

(73) Assignee: Tyber Medical LLC, Bethlehem, PA (US)

( * ) Notice: Subject to any disclaimer, the term of this patent is extended or adjusted under 35 U.S.C. 154(b) by 406 days.

(21) Appl. No.: 18/234,428

(22) Filed: Aug. 16, 2023

(65) Prior Publication Data

US 2024/0074790 A1     Mar. 7, 2024

Related U.S. Application Data

(60) Provisional application No. 63/402,964, filed on Sep. 1, 2022.

(51) Int. Cl.
*A61B 17/68*     (2006.01)
*A61B 17/15*     (2006.01)
(Continued)

(52) U.S. Cl.
CPC .............. *A61B 17/68* (2013.01); *A61B 17/15* (2013.01); *A61B 17/151* (2013.01); *A61B 17/152* (2013.01); *A61B 17/1682* (2013.01); *A61B 17/1703* (2013.01); *A61B 17/1717* (2013.01); *A61B 17/1725* (2013.01); *A61B 17/1728* (2013.01); *A61B 17/1732* (2013.01); *A61B 17/1735* (2013.01); *A61B 17/1739* (2013.01); *A61B 17/1775* (2016.11); *A61B 2017/320052* (2013.01); *A61B 2017/564* (2013.01); *A61B 17/66* (2013.01); *A61B 2017/681* (2013.01);
(Continued)

(58) Field of Classification Search
CPC ... A61B 17/1775; A61B 17/68; A61B 17/848; A61B 17/8866; A61B 17/17; A61B 17/0482; A61B 17/1703; A61B 17/1717; A61B 17/1728; A61B 17/1732; A61B 17/1725; A61B 17/1735; A61B 17/1739; A61B 17/8897; A61B 17/90; A61B 17/15; A61B 17/151; A61B 17/152; A61B 17/56; A61B 17/58; A61B 17/86; A61B 17/842; A61B 17/8872; A61B 17/1682; A61B 17/16; A61B 17/66; A61B 17/808; A61B 2017/681; A61B 2017/320052; A61B 2017/564; A61F 2/0805; A61F 2/30749; A61F 2/4202; A61F 2/42; A61F 2/46; A61F 2/4603; A61F 2/4606; A61F 2002/4207; A61F 2002/0841; A61F 2002/4677; A61F 2002/4687
USPC .......... 606/98, 104, 87, 53, 79–80, 86 R, 96
See application file for complete search history.

(56) References Cited

U.S. PATENT DOCUMENTS

| | | | | |
|---|---|---|---|---|
| 4,901,711 A | * | 2/1990 | Goble | ................ A61B 17/1714 606/97 |
| 2010/0191243 A1 | * | 7/2010 | Horan | .................... A61B 17/15 606/87 |
| 2021/0113222 A1 | * | 4/2021 | Khatibi | .............. A61B 17/1775 |

* cited by examiner

*Primary Examiner* — Marcela I. Shirsat
(74) *Attorney, Agent, or Firm* — Joseph E. Maenner; Maenner & Associates, LLC

(57) ABSTRACT

A talar repair jig includes an elongate base extending along a longitudinal axis. The base has a front face, a first side opening through the front face, wherein the first opening supports a first rod assembly, a second side opening through the front face, distal from the first side opening, wherein the second side opening supports a second rod assembly, and a central opening extending through the front face, wherein the central opening supports a pair of rear alignment guides.

11 Claims, 4 Drawing Sheets

(51) Int. Cl.

| | |
|---|---|
| *A61B 17/16* | (2006.01) |
| *A61B 17/17* | (2006.01) |
| *A61B 17/32* | (2006.01) |
| *A61B 17/56* | (2006.01) |
| *A61B 17/66* | (2006.01) |
| *A61B 17/84* | (2006.01) |
| *A61B 17/86* | (2006.01) |
| *A61B 17/88* | (2006.01) |
| *A61B 17/90* | (2006.01) |
| *A61F 2/08* | (2006.01) |
| *A61F 2/42* | (2006.01) |
| *A61F 2/46* | (2006.01) |

(52) U.S. Cl.
CPC ............. *A61B 17/848* (2013.01); *A61B 17/86* (2013.01); *A61B 17/8866* (2013.01); *A61B 17/8872* (2013.01); *A61B 17/8897* (2013.01); *A61B 17/90* (2021.08); *A61F 2/0805* (2013.01); *A61F 2002/0841* (2013.01); *A61F 2/4202* (2013.01); *A61F 2002/4207* (2013.01); *A61F 2/4606* (2013.01); *A61F 2002/4677* (2013.01)

113

100

110

111

132

110

122

120

124

180

130

118    116

114    152    170    170    112    132    180

110

113    119    172    130

150    172

152    132

180

TALAR REPAIR JIG

BACKGROUND OF THE INVENTION

Field of the Invention

The invention relates to a jig that can be used to repair a fractured talar bone.

Description of the Related Art

Presently, talar fractures are repaired by inserting anterior/posterior (A/P) screws and even plates, requiring invasive procedures that can lead to subsequent infections. Additionally, A/P screws can result in non-union and mal-union of the fractured bone pieces.

It would be beneficial to provide a talar repair jig that is adjustable in both the axial and coronal directions, and can account for medial and lateral communition.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a talar repair jig that includes an elongate base extending along a longitudinal axis. The base has a front face, a first side opening through the front face, wherein the first opening supports a first rod assembly, a second side opening through the front face, distal from the first side opening, wherein the second side opening supports a second rod assembly, and a central opening extending through the front face, wherein the central opening supports a pair of rear alignment guides.

In an alternative embodiment, the present invention provides a talar repair jig comprising an elongate base extending along a longitudinal axis and a pair of rear alignment guides extending from the base. The rear alignment guides are each separately translatable along a guide longitudinal axis. A rod assembly extends from the base on either side of the pair of rear alignment guides. The rod assemblies are translatable along the longitudinal axis of the base.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION

Figure 1:
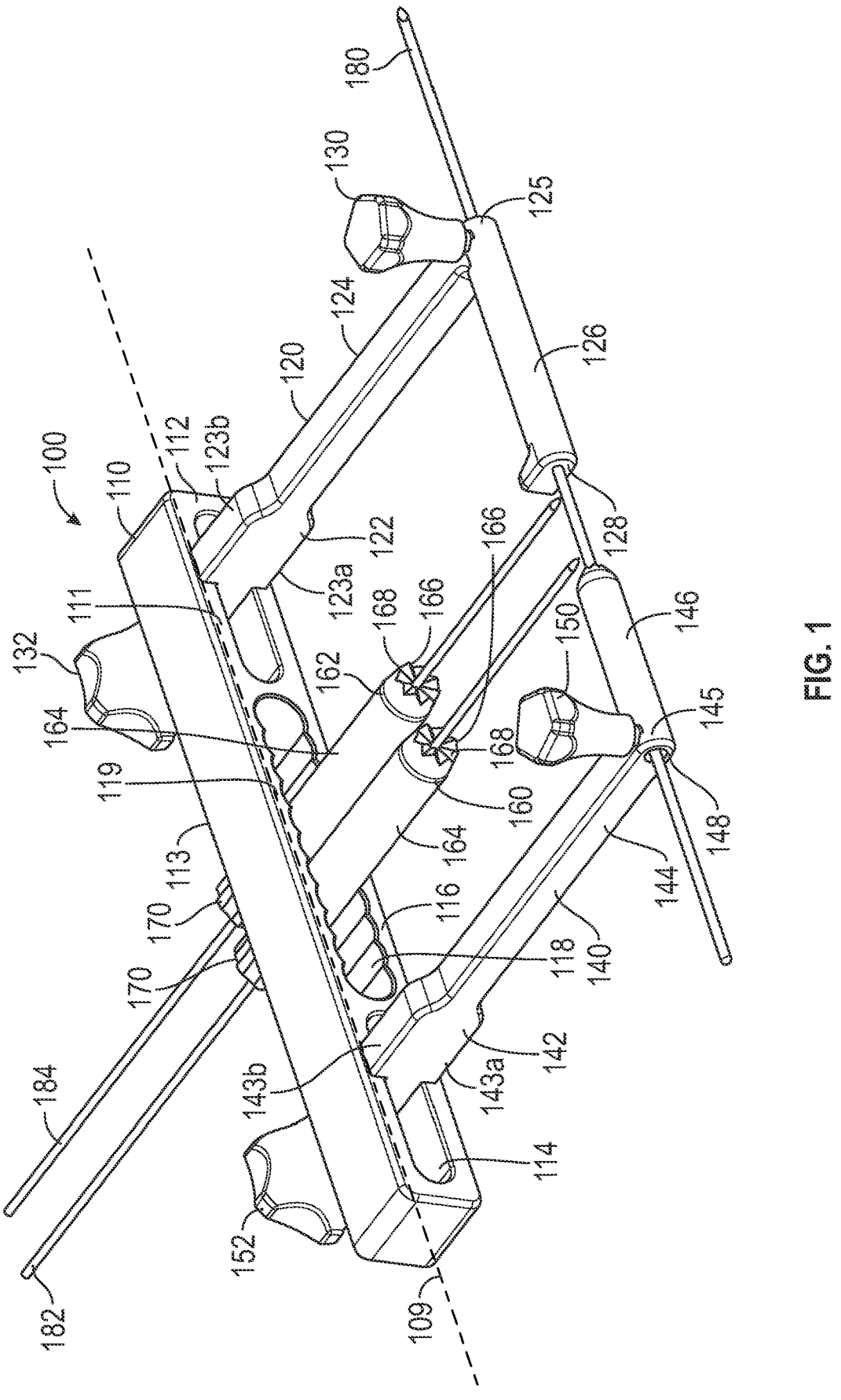
FIG. 1 is a perspective view of a talar repair jig according to an exemplary embodiment of the present invention.
Figures 2, 3, 4, 5:
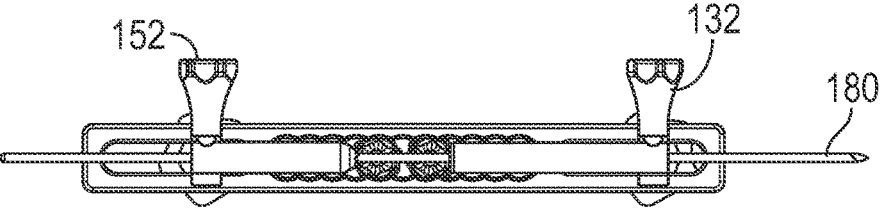
FIG. 2 is a top plan view of the jig of FIG. 1.
FIG. 3 is an end elevational view of the jig of FIG. 1.
FIG. 4 is an opposite end elevational view of the jig of FIG. 1.
FIG. 5 is a side elevational view of the jig of FIG. 1.

U.S. Provisional Patent Application Ser. No. 63/402,961, entitled "Ligament/Tendon Suture with Paired Anchor System", filed on Sep. 1, 2022 and invented by this inventor; U.S. Provisional Patent Application Ser. No. 63/402,962, entitled "Screw Capture System for Calcaneal Fracture", filed on Sep. 1, 2022 and invented by this inventor; U.S. Provisional Patent Application Ser. No. 63/402,965, entitled "Screw Blade Capture System", filed on Sep. 1, 2022 and invented by this inventor; U.S. Provisional Patent Application Ser. No. 63/402,967, entitled "Repair Plate System from Inside/Out", filed on Sep. 1, 2022 and invented by this inventor; U.S. Provisional Patent Application Ser. No. 63/402,971, entitled "Syndesmosis Repair Jig System and Method of Use", filed on Sep. 1, 2022 and invented by this inventor; U.S. Provisional Patent Application Ser. No. 63/402,969, entitled "Distal Tibial Osteotomy System", filed on Sep. 1, 2022 and invented by this inventor; U.S. Provisional Patent Application Ser. No. 63/402,963, entitled "External Fixation System", filed on Sep. 1, 2022 and invented by this inventor; and U.S. Provisional Patent Application Ser. No. 63/402,970, entitled "Achilles Tendon Repair Jig", filed on Sep. 1, 2022 and invented by this inventor, are all incorporated herein by reference in their entireties.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

The present invention is a jig for repairing a talar fracture. Referring to FIGS. 1-4, a jig 100 according to an exemplary embodiment of the present invention is shown.

Jig 100 includes an elongate base 110 extending along a longitudinal axis 109, the base 110 having a front face 111, a rear face 113, and plurality of elongate through openings formed therein extending between front face 111 and rear face 113. A first side opening 112 supports a first rod assembly 120. A second side opening 114, distal from side opening 112 supports a second rod assembly 140. A central opening 116 supports a pair of rear alignment guides 160, 162. Central opening 116 can have scalloped top and bottom faces 118, 119, respectively, to support rear alignment guides 160, 162 and prevent rear alignment guides 160, 162 from sliding medially and laterally toward either of side openings 112, 114. Each rear alignment guide 160, 162 is removable from base 110 and translated in a direction parallel to the longitudinal axis 109 to a desired location, and then re-inserted into central opening 116.

Rod assembly 120 includes an elongate arm 122 that extends perpendicular to base 110. Arm 122 has a wide base engaging portion 122 with flanges 123a, 123b, (anatomically matched to the segment of the Talar neck), that engage a face 111 of base 110. Arm 122 necks down to a narrower portion 124 and terminates at an end 125. A cannulated K-wire guide 126 extends perpendicularly to arm 122 and parallel to longitudinal axis 109. Guide 126 has a through opening 128 to allow a K-wire 180 to pass therethrough.

A securing device 130 at end 125 can releasably secure K-wire 180 within through opening 128. Securing device 130 can be a threaded knob that can be screwed downwardly to provide a frictional interference, forcing K-wire 180 against a far wall of through opening 128.

Arm 122 can be secured to base 110 via a securing device 132. Securing device 132 can be a threaded knob that can be screwed toward arm 122 to provide a frictional interference, forcing arm 122 against front face 111 of base 110. When securing device is loose, first arm 110 can slide along the length of first side opening 112 to a desired location.

Similar to first rod assembly 120, second rod assembly 140 includes an elongate arm 142 that extends perpendicular to base 110. Arm 142 has a wide base engaging portion 142 with flanges 143a, 143b that engage a face 111 of base 110. Arm 142 necks down to a narrower portion 144 and terminates at an end 145. A cannulated K-wire guide 146 extends perpendicularly to arm 142 and parallel to longitudinal axis 109. Guide 146 has a through opening 148 to allow K-wire 180 to pass therethrough.

A securing device 150 at end 145 can releasably secure K-wire 180 within through opening 148. Securing device 150 can be a threaded knob that can be screwed downwardly to provide a frictional interference, forcing K-wire 180 against a far wall of through opening 148.

Arm 142 can be secured to base 110 via a securing device 152. Securing device 152 can be a threaded knob that can be screwed toward arm 142 to provide a frictional interference, forcing arm 142 against front face 111 of base 110. When securing device is loose, second arm 130 can slide along the length of first side opening 112 to a desired location.

Rear alignment guides 160, 162 each include a cannulated tubular body 164 with a through opening 166 formed therein. Through openings 166 are sized to allow K-wires 182, 184, respectively, to be inserted therethrough.

Distal ends 168 of guides 160, 162 each have pointed contoured members that allow guides 160, 162 to grip into a talus bone 52 during use. Textured stop members 170 are provided at proximal ends 172 of guides 160, 162 to provide a gripping surface for a clinician. Proximal ends 172 have a larger diameter than the height of central opening 116 so that guides 160, 162 are stopped from distal movement by proximal ends 172 engaging rear face 113 of base 110.

Figure 6:
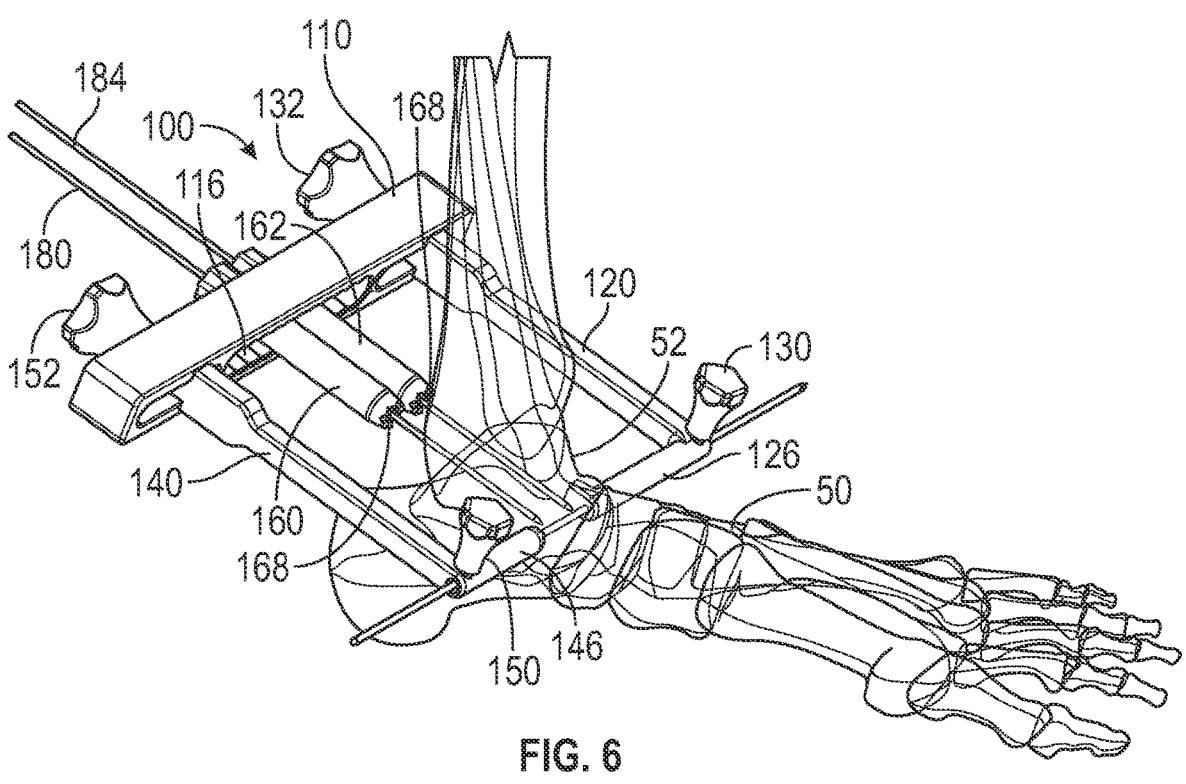
FIG. 6 is a perspective view of the jig of FIG. 1 used on a foot.
Figure 7:
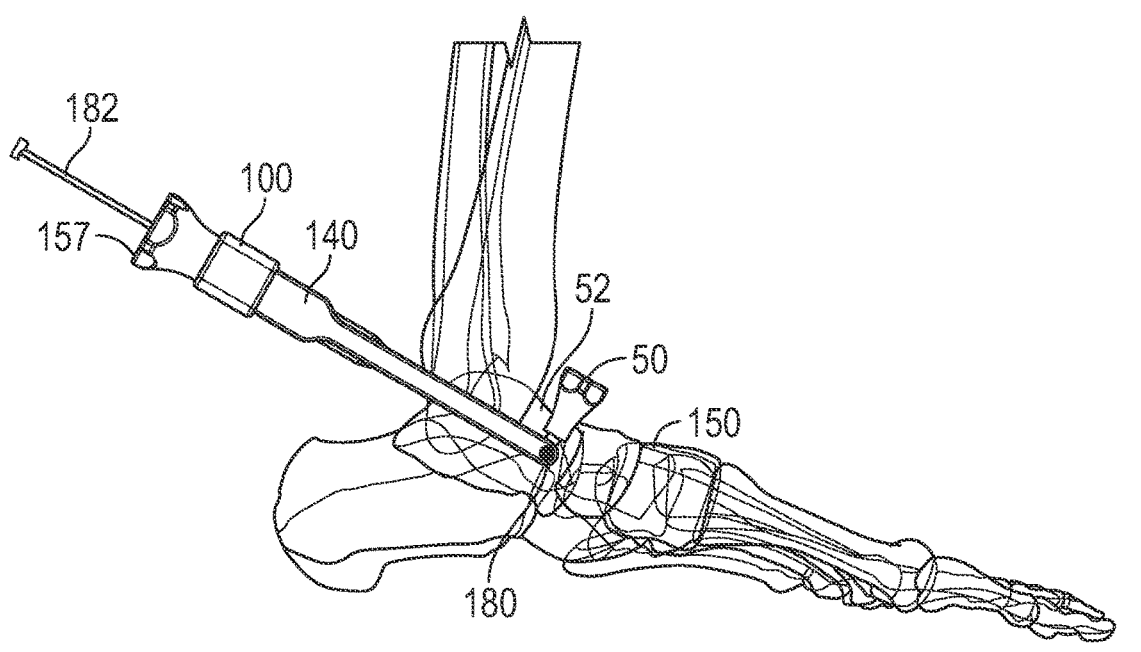
FIG. 7 is a side elevational view of the jig of FIG. 1 attached to the foot of FIG. 6.
Figure 8:
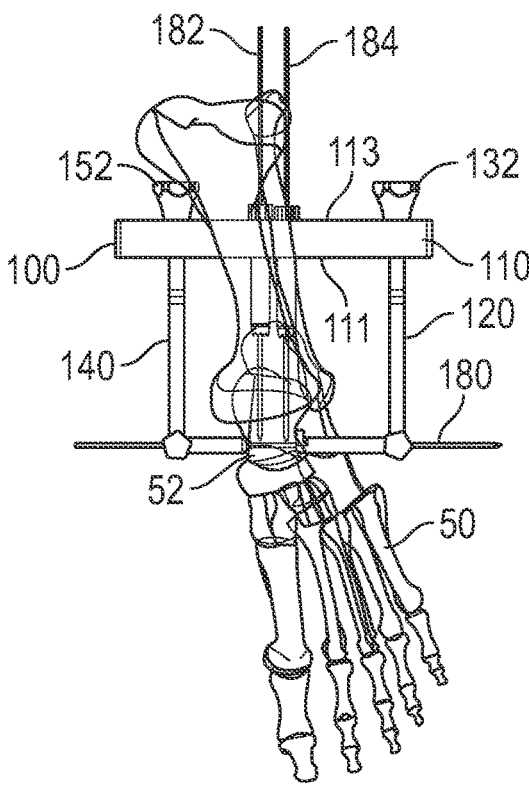
FIG. 8 is a top plane view of the jig of FIG. 1 attached to the foot of FIG. 6.
Figure 9:
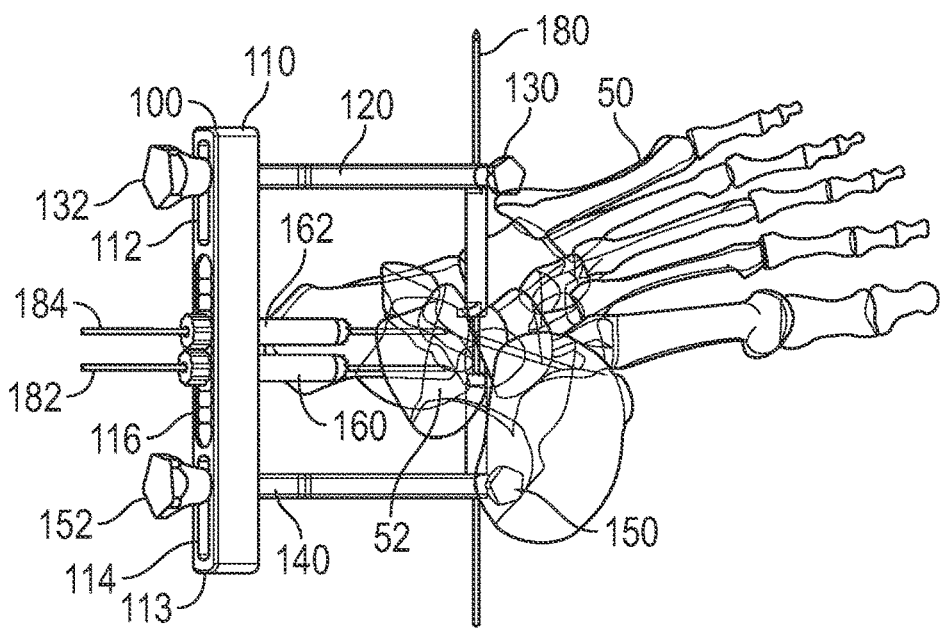
FIG. 9 is a rear perspective view of the jig of FIG. 1 attached to the foot of FIG. 6.

FIGS. 6-9 show jig 100 attached to a foot 50 to secure the talus 52 of foot 50. To use jig 100, jig 100 is placed around a foot as shown in FIG. 6. Arms 120, 140 are compressed toward each other to grip talus between K-wire guides 126, 146 and secured in place by tightening securing members 132, 152. K-wire 180 is then inserted through guide 146, through talus 52, and then through guide 126. K-wire 180 is secured to jig 100 by tightening securing members 130, 150. K-wire 180 becomes an axis about which a remainder of jig 100 can pivot.

Jig 100 can be pivoted about K-wire 180 to a desired position. When jig 100 is in place, guides 160, 162 are inserted into desired locations in central opening 116 and advanced distally so that distal ends 168 of guides 160, 162 can bite into foot 50. K-wires 182, 184 are then advanced through guides 160, 162, respectively, and into talus 52. With K-wires 180, 182 installed, K-wire 180 is removed and jig 100 is removed, leaving K-wires 182, 184. Jig 100 is left on until the screws (not shown) are in place. Cannulated screws (not shown) can then be threaded over K-wires 182, 184 and screwed into talus 152 to secure talus 152.

It will be further understood that various changes in the details, materials, and arrangements of the parts which have been described and illustrated in order to explain the nature of this invention may be made by those skilled in the art without departing from the scope of the invention as expressed in the following claims.

What is claimed is:
1. A talar repair jig comprising:
an elongate base extending along a longitudinal axis, the base having:
a front face;
a rear face;
a first side opening extending through the base between the front face and the rear face, the first opening supporting a first rod assembly; and
a second side opening extending through the base between the front face and the rear face, distal from the first side opening, the second side opening supporting a second rod assembly;
a pair of rear alignment guides; and
the base further having a central opening extending through the base between the front face and the rear face, the central opening supporting the pair of rear alignment guides,
wherein the central opening comprises scalloped top and bottom faces to support the rear alignment guides and the prevent rear alignment guides from sliding medially and laterally toward either of the first or second side openings.

2. The talar repair jig according to claim 1, wherein the first rod assembly comprises a first elongate arm extending perpendicular to the longitudinal axis.

3. The talar repair jig according to claim 2, wherein the first elongate arm comprises a base engaging portion comprising upper and lower flanges engaging the front face of the base.

4. The talar repair jig according to claim 3, wherein the first elongate arm necks down from the flanges and terminates at a first K-wire guide extending perpendicularly to the first elongate arm and parallel the longitudinal axis, the first K-wire guide having a first through opening extending longitudinally therethrough.

5. The talar repair jig according to claim 4 wherein a first K-wire extends through the first K-wire guide and a securing device releasably secures the K-wire within the first through opening.

6. The talar repair jig according to claim 4, further comprising a first arm securing device configured to releasably secure the first elongate arm to the base.

7. The talar repair jig according to claim 4, wherein the second rod assembly includes a second elongate arm extending perpendicular to the longitudinal axis and terminating at a second K-wire guide extending perpendicularly to the second elongate arm and parallel to the longitudinal axis.

8. The talar repair jig according to claim 7, wherein the second K-wire guide has a second through opening configured to allow the first K-wire to pass therethrough.

9. The talar repair jig according to claim 1, wherein the rear alignment guides each include a tubular body having a guide through opening formed therein.

10. The talar repair jig according to claim 1, wherein the rear alignment guides each have a distal end having pointed contoured members configured to grip into a talus bone during use.

11. The talar repair jig according to claim 1, wherein the rear alignment guides each have a proximate end having a larger diameter than a height of the central opening such that the rear alignment guides are stopped from distal movement by the proximal ends engaging the rear face of the base.

* * * * *